(12) United States Patent
Frazier

(10) Patent No.: US 11,240,978 B2
(45) Date of Patent: Feb. 8, 2022

(54) HEMP VARIETY NBS CBD-1

(71) Applicant: Phylos Bioscience, Portland, OR (US)

(72) Inventor: Harold Frazier, Cottage Grove, OR (US)

(73) Assignee: Phylos Bioscience, Inc., Portland, OR (US)

( * ) Notice: Subject to any disclaimer, the term of this patent is extended or adjusted under 35 U.S.C. 154(b) by 7 days.

(21) Appl. No.: 16/911,305

(22) Filed: Jun. 24, 2020

(65) Prior Publication Data

US 2020/0329658 A1    Oct. 22, 2020

Related U.S. Application Data

(60) Provisional application No. 62/938,768, filed on Nov. 21, 2019.

(51) Int. Cl.
    *A01H 6/28*    (2018.01)
    *A01H 5/12*    (2018.01)

(52) U.S. Cl.
    CPC ................. *A01H 6/28* (2018.05); *A01H 5/12* (2013.01)

(58) Field of Classification Search
    CPC ....................................................... A01H 6/28
    See application file for complete search history.

(56) References Cited

U.S. PATENT DOCUMENTS

2018/0295804 A1* 10/2018 Muck ...................... A01H 5/02

OTHER PUBLICATIONS

PVP Application No. 201900403.

* cited by examiner

*Primary Examiner* — Weihua Fan
(74) *Attorney, Agent, or Firm* — Gregory Ellis

(57) ABSTRACT

The present invention discloses a hemp plant variety designated NBS CBD-1. The cultivar is a feminized, autoflowering, high CBD hemp variety. The plant and products thereof can be useful for a variety of medicinal uses, including movement disorders, anxiety, and pain, as well as a variety of industrial uses. Also provided are tissues cultures, seeds, and plant cells of the NBS CBD-1 variety.

11 Claims, 5 Drawing Sheets

US 11,240,978 B2

HEMP VARIETY NBS CBD-1

BACKGROUND OF THE INVENTION

*Cannabis* plants contain over a hundred known cannabinoids, which bind to endogenous endocannabinoid receptors. Once such cannabinoid is cannabidiol (CBD), which is a homologue of tetrahydrocannabinol (THC) with a unique pharmacological profile and distinct molecular targets.

CBD promises potential benefits across a broad set of applications. *Cannabis* strains or extracts with high CBD levels can be used as an agent for a variety of conditions including movement disorders, anxiety, and pain. In 2018 the United States Food and Drug Administration approved the CBD drug Epidiolex for the treatment of specific epilepsy disorders.

Research and development as well as the sale of CBD products has been limited because *Cannabis* is a Schedule I controlled substance in the United States. Hemp, which is *Cannabis* having less than 0.3% total THC, was descheduled with passage of the 2018 Farm Bill. There currently exists an enormous need for hemp strains having high CBD levels to unlock the potential of CBD. The invention described herein fulfills this need. Provided herein is NBS CBD-1: a feminized, autoflowering, high CBD hemp variety.

SUMMARY OF THE INVENTION

The present teachings relate to a hemp plant variety designated NBS CBD-1, and parts and offspring of that variety, having high CBD levels. In an embodiment, a hemp plant of variety designated NBS CBD-1 is provided.

In an embodiment, a seed of a hemp plant variety designated NBS CBD-1 is provided. In an embodiment the seed further comprises a trait introduced by backcrossing or genetic transformation.

In an embodiment, a hemp plant is provided. The hemp plant comprises at least one plant cell produced by growing the seed of a hemp plant variety designated NBS CBD-1.

In an embodiment an F1 hybrid seed is provided. The hybrid seed is produced by crossing the hemp plant of variety NBS CBD-1 with a different hemp plant.

In an embodiment, an F1 hybrid plant or plant part grown from a seed of an F1 hybrid of a plant of variety NBS CBD-1 is provided. In an embodiment the plant part comprises at least one cell of the F1 hybrid plant.

In an embodiment, an An F2-F7 hybrid seed produced by crossing the F1 hybrid plant of claim 6 with different hemp plants. In an embodiment, an F2-F7 hybrid plant grown from the seeds of claim 7, or a plant part thereof, the plant part comprising at least one cell of the F2-F7 hybrid plant.

In an embodiment a tissue culture of cells is provided. The tissue culture of cells is produced from a hemp plant of the variety NBS CBD-1. In an embodiment a hemp plant generated from the tissue culture of cells is provided, wherein the plant has all of the morphological and physiological characteristics of variety NBS CBD-1.

In an embodiment a protoplast is provided. The protoplast is produced from a hemp plant of the variety NBS CBD-1.

In an embodiment a method of generating processed hemp is provided. The method comprises the use of a plant of the variety NBS CBD-1. In an embodiment of the hemp product is a CBD product.

In an embodiment a hemp product is provided. The hemp product is produced using a plant of the variety NBS CBD-1. In an embodiment the hemp product is a CBD product.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION OF THE INVENTION

Figure 1:
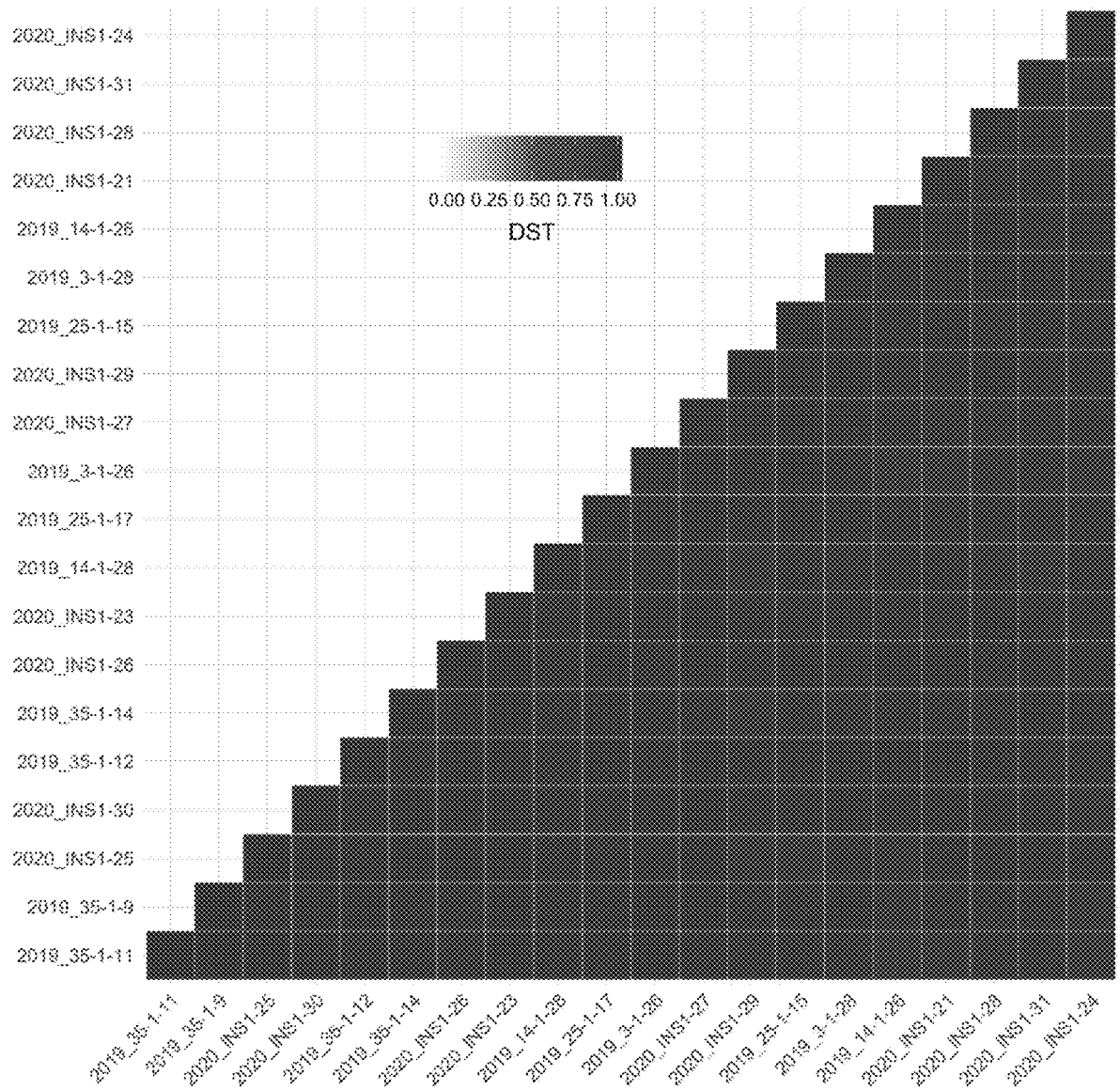
FIG. 1 illustrates pairwise genetic distance for a collection of twenty NBS CBD-1 samples, each of which are described on both the X and Y axes.

The present teachings describe NBS CBD-1: a feminized, autoflowering, high CBD hemp variety. These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The terminology used in the disclosure herein is for the purpose of describing particular embodiments only and is not intended to be limiting of the disclosure. As used in the description of the embodiments of the disclosure and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, amount, dose, time, temperature, for example, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs.

Definitions

The term "acidic cannabinoid" refers to a cannabinoid having one or more carboxylic acid functional groups. Examples of acidic cannabinoids include, but are not limited to, cannabidiolic acid (CBDA), acid tetrahydrocannabinolic acid (THCA), cannabidiolic acid (CBDA), tetrahydrocannabivarinic acid (TCHVA), and cannabichromenic acid (CBC). Acidic cannabinoids are frequently the predominant cannabinoids found in raw (i.e., unprocessed) *Cannabis* plant material.

The term "backcrossing" refers to a process in which a breeder crosses progeny back to one of the parents one or more times, for example, a first generation hybrid F1 with one of the parental genotype of the F1 hybrid.

The term "*Cannabis*" refers to plants of the genus *Cannabis*, including *Cannabis sativa, Cannabis indica*, and *Cannabis ruderalis.*

The term "*Cannabis* oil" refers to a mixture of compounds obtained from the extraction of *Cannabis* plants. Such compounds include, but are not limited to, cannabinoids, terpenes, terpenoids, and other compounds found in the *Cannabis* plant. The exact composition of *Cannabis* oil will depend on the strain of *Cannabis* that is used for extraction, the efficiency and process of the extraction itself, and any additives that might be incorporated to alter the palatability or improve administration of the *Cannabis* oil.

The term "cell" includes a plant cell, whether isolated, in tissue culture, or incorporated in a plant or plant part.

The term "CBD" refers to cannabidiol. The term "CBDA" refers to cannabidiolic acid.

The term "cross", "crossing", "cross pollination" or "cross-breeding" refer to the process by which the pollen of one flower on one plant is applied (artificially or naturally) to the ovule (stigma) of a flower on another plant. Backcrossing is a process in which a breeder repeatedly crosses hybrid progeny, for example a first generation hybrid (F1), back to one of the parents of the hybrid progeny. Backcrossing can be used to introduce one or more single locus conversions from one genetic background into another.

The term "cultivar" means a group of similar plants that by structural features and performance (e.g., morphological and physiological characteristics) can be identified from other varieties within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

The term "donor plants" refer to the parents of a variety which contains the gene or trait of interest which is desired to be introduced into a second variety (e.g., "recipient plants").

The term "extract" refers to a solution that has been purged or dehydrated to remove residual solvent. In the methods of the invention, the extract is formed by purging or dehydrating the distillate using any known means in the art.

The term "hybrid" refers to a variety or cultivar that is the result of a cross of plants of two different varieties. An exemplary hybrid would be a plant that is the result of a cross between NBS CBD-1 and a second hemp plant. A hybrid, as described here, can refer to plants that are genetically different at any particular loci. A hybrid can further include a plant that is a variety that has been bred to have at least one different characteristic from the parent, e.g., a progeny plant created from a cross between NBS CBD-1 and another plant wherein the hybrid progeny has at least one phenotypic characteristic that is different from the NBS CBD-1 variety. "F1 hybrid" refers to the first generation hybrid, "F2 hybrid" the second generation hybrid, "F3 hybrid" the third generation, and so on.

The term "genotype" refers to the genetic makeup of an individual cell, cell culture, tissue, organism (e.g., a plant), or group of organisms.

As used herein, the term "inbreeding" refers to the production of offspring via the mating between relatives. The plants resulting from the inbreeding process are referred to herein as "inbred plants" or "inbreds."

As used herein, a "landrace" refers to a local variety of a domesticated plant species which has developed largely by natural processes, by adaptation to the natural and cultural environment in which it lives. The development of a landrace may also involve some selection by humans but it differs from a formal breed which has been selectively bred deliberately to conform to a particular formal, purebred standard of traits.

The term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

The term "neutral cannabinoid" refers to a cannabinoid without carboxylic acid functional groups. Examples of neutral cannabinoids include, but are not limited to, THC, THCV, CBD, CBG, CBC, and CBN.

The term "offspring" refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait) and may include offspring with different phenotypic characteristics, while an F2 may be (and usually is) an offspring resulting from self-pollination of said F1 hybrids.

The present disclosure provides ovules and pollens of plants. As used herein when discussing plants, the term "ovule" refers to the female gametophyte, whereas the term "pollen" means the male gametophyte.

The term "plant" refers to whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks. Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root. A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein. In an embodiment described herein are plants in the genus of *Cannabis* and plants derived thereof, which can be produced asexual or sexual reproduction.

The term "plant part" or "plant tissue" refers to any part of a plant including but not limited to, an embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen. Plant part may also include certain extracts such as kief, oil, or hash which includes *Cannabis* trichomes or glands.

The term "progeny" refers to any plant resulting from a vegetative or sexual reproduction from one or more parent plants or descendants thereof. For instance a progeny plant may be obtained by cloning or selfing of a parent plant or by crossing two parent plants and include selfings as well as the F1 or F2 or still further generations. An F1 is a first-generation progeny produced from parents at least one of which is used for the first time as donor of a trait, while offspring of second generation (F2) or subsequent generations (F3, F4, etc.) are specimens produced from selfings of F1's F2's etc. An F1 may thus be (and usually is) a hybrid resulting from a cross between two true breeding parents (true-breeding is homozygous for a trait) and may include F1 hybrids with new phenotypic characteristics, while an F2 may be (and usually is) an progeny resulting from self-pollination of said F1 hybrids.

The term "protoplast" as used herein refers to an entire plant cell, excluding the cell wall.

The term "sample" includes a sample from a plant, a plant part, a plant cell, or from a transmission vector, or a soil, water or air sample.

The term "secondary metabolites" as used herein refers to organic compounds that are not directly involved in the normal growth, development, or reproduction of an organism. In other words, loss of secondary metabolites does not result in immediate death of said organism.

The term "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

The term "tissue culture" refers to a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference The term "transformant" refers to a cell, tissue or organism that has undergone transformation. The original transformant is designated as "T0" or "T0." Selfing the T0 produces a first transformed generation designated as "T1" or "T1."

The term "transformation" refers to the transfer of nucleic acid (i.e., a nucleotide polymer) into a cell. As used herein, the term "genetic transformation" refers to the transfer and incorporation of DNA, especially recombinant DNA, into a cell.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

*Cannabis*, Hemp, and CBD

*Cannabis* has long been used for drug and industrial purposes, fiber (hemp), for seed and seed oils, for medicinal purposes, and for recreational purposes. Industrial hemp products are made from *Cannabis* plants selected to produce an abundance of fiber. Some *Cannabis* strains have been bred to produce minimal levels of THC, the principal psychoactive constituent responsible for the psychoactivity associated with marijuana. Marijuana has historically consisted of the dried flowers of *Cannabis* plants selectively bred to produce high levels of THC and other psychoactive cannabinoids. Various extracts including hashish and hash oil are also produced from the plant.

*Cannabis* is an annual, dioecious, flowering herb. The leaves are palmately compound or digitate, with serrate leaflets. *Cannabis* normally has imperfect flowers, with staminate "male" and pistillate "female" flowers occurring on separate plants. It is not unusual, however, for individual plants to separately bear both male and female flowers (i.e., have monoecious plants). Although monoecious plants are often referred to as "hermaphrodites," true hermaphrodites (which are less common in *Cannabis*) bear staminate and pistillate structures on individual flowers, whereas monoecious plants bear male and female flowers at different locations on the same plant.

The life cycle of *Cannabis* varies with each variety but can be generally summarized into germination, vegetative growth, and reproductive stages. Because of heavy breeding and selection by humans, most *Cannabis* seeds have lost dormancy mechanisms and do not require any pre-treatments or winterization to induce germination (See Clarke, R C et al. "*Cannabis*: Evolution and Ethnobotany" University of California Press 2013). Seeds placed in viable growth conditions are expected to germinate in about 3 to 7 days. The first true leaves of a *Cannabis* plant contain a single leaflet, with subsequent leaves developing in opposite formation, with increasing number of leaflets. Leaflets can be narrow or broad depending on the morphology of the plant grown. *Cannabis* plants are normally allowed to grow vegetatively for the first 4 to 8 weeks. During this period, the plant responds to increasing light with faster and faster growth. Under ideal conditions, *Cannabis* plants can grow up to 2.5 inches a day, and are capable of reaching heights of up to 20 feet. Indoor growth pruning techniques tend to limit *Cannabis* size through careful pruning of apical or side shoots.

Some *Cannabis* varieties will flower without the need for external stimuli, most varieties have an absolute requirement for inductive photoperiods in the form of short days or long nights to induce fertile flowering. The first sign of flowering in *Cannabis* is the appearance of undifferentiated flower primordial along the main stem of the nodes. At this stage, the sex of the plants are still not distinguishable. As the flower primordia continue to develop, female (pistillate), and male (staminate) flowers can be distinguished.

For most cannabinoid producing purposes, only female plants are desired. The presence of male flowers is considered undesirable as pollination is known to reduce the cannabinoid yield, and potentially ruin a crop. For this reason, most *Cannabis* is grown "sinsemilla" through vegetative (i.e., asexual) propagation. In this way, only female plants are produced and no space is wasted on male plants.

*Cannabis* is diploid, having a chromosome complement of 2n=20, although polyploid individuals have been artificially produced. The first genome sequence of *Cannabis*, which is estimated to be 820 Mb in size, was published in 2011 by a team of Canadian scientists (Bakel et al, "The draft genome and transcriptome of *Cannabis sativa*" Genome Biology 12:R102).

All known strains of *Cannabis* are wind-pollinated and the fruit is an achene. Most strains of *Cannabis* are short day plants, with the possible exception of *C. sativa* subsp. *sativa* var. *spontanea* (=*C. ruderalis*), which is commonly described as "auto-flowering" and may be day-neutral.

The genus *Cannabis* was formerly placed in the Nettle (Urticaceae) or Mulberry (Moraceae) family, and later, along with the *Humulus* genus (hops), in a separate family, the Hemp family (Cannabaceae sensu stricto). Recent phylogenetic studies based on cpDNA restriction site analysis and gene sequencing strongly suggest that the Cannabaceae sensu stricto arose from within the former Celtidaceae family, and that the two families should be merged to form a single monophyletic family, the Cannabaceae sensu lato.

*Cannabis* plants produce a unique family of terpenophenolic compounds called cannabinoids. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the *Cannabis* plant (Rudolf Brenneisen, 2007, Chemistry and Analysis of Phytocannabinoids (cannabinoids produced produced by *Cannabis*) and other *Cannabis* Constituents, In Marijuana and the Cannabinoids, ElSohly, ed.; incorporated herein by reference) and at least 85 different cannabinoids have been isolated from the plant (El-Alfy, Abir T, et al., 2010, "Antidepressant-like effect of delta-9-tetrahydrocannabinol and other cannabinoids isolated from *Cannabis sativa* L", Pharmacology Biochemistry and Behavior 95 (4): 434-42; incorporated herein by reference). The two cannabinoids usually produced in greatest abundance are cannabidiol (CBD) and/or $\Delta^9$-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in marijuana.

Hemp is non-psychoactive and legally defined in the United States as *Cannabis* having less than 0.3% total THC (THCA+THC). For instruments that detect THCA levels without heat, e.g., HPLC, the THCA is not decarboxylated. Consequently, total THC levels using HPLC can be determined by multiplying the THCA levels by 87.7%, which equals the molecular weight of THCA minus its carboxyl group. For instruments that detect THCA levels using heat, e.g., gas chromatography, complete decarboxylation is presumed to have occurred and consequently, total THC is determined without multiplying THCA levels by 87.7%.

Hemp's utility can be refined into a variety of commercial and industrial items, including paper, textiles, clothing, biodegradable plastics, paint, insulation, biofuel, food, and animal feed. Hemp can also be used to produce CBD.

Cannabinoids are the most studied group of secondary metabolites in *Cannabis*. Most exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008). The biologically active forms for human consumption are the neutral forms. Decarboxylation is usually achieved by thorough drying of the plant material followed by heating it, often by either combustion, vaporization, or heating or baking in an oven. Unless otherwise noted, references to cannabinoids in a plant include both the acidic and decarboxylated versions (e.g., CBD and CBDA).

Detection of neutral and acidic forms of cannabinoids are dependent on the detection method utilized. Two popular detection methods are high-performance liquid chromatography (HPLC) and gas chromatography (GC). HPLC separates, identifies, and quantifies different components in a mixture, and passes a pressurized liquid solvent containing the sample mixture through a column filled with a solid adsorbent material. Each molecular component in a sample mixture interacts differentially with the adsorbent material, thus causing different flow rates for the different components and therefore leading to separation of the components. In contrast, GC separates components of a sample through vaporization. The vaporization required for such separation occurs at high temperature. Thus, the main difference between GC and HPLC is that GC involves thermal stress and mainly resolves analytes by boiling points while HPLC does not involve heat and mainly resolves analytes by polarity. The consequence of utilizing different methods for cannabinoid detection therefore is that HPLC is more likely to detect acidic cannabinoid precursors, whereas GC is more likely to detect decarboxylated neutral cannabinoids.

The cannabinoids in *Cannabis* plants include, but are not limited to, $\Delta$9-Tetrahydrocannabinol ($\Delta^9$-THC), $\Delta^8$-Tetrahydrocannabinol ($\Delta^8$-THC), Cannabichromene (CBC), Cannabicyclol (CBL), Cannabidiol (CBD), Cannabielsoin (CBE), Cannabigerol (CBG), Cannabinidiol (CBND), Cannabinol (CBN), Cannabitriol (CBT), and their propyl homologs, including, but are not limited to cannabidivarin (CBDV), $\Delta^9$-Tetrahydrocannabivarin (THCV), cannabichromevarin (CBCV), and cannabigerovarin (CBGV). See Holley et al. (Constituents of *Cannabis sativa* L. XI Cannabidiol and cannabichromene in samples of known geographical origin, J. Pharm. Sci. 64:892-894, 1975) and De Zeeuw et al. (Cannabinoids with a propyl side chain in *Cannabis*, Occurrence and chromatographic behavior, Science 175:778-779), each of which is herein incorporated by reference in its entirety for all purposes. Non-THC cannabinoids can be collectively referred to as "CBs", wherein CBs can be one of THCV, CBDV, CBGV, CBCV, CBD, CBC, CBE, CBG, CBN, CBND, and CBT cannabinoids.

CBD promises potential benefits across a broad set of applications. *Cannabis* strains or extracts with high CBD levels can be used as an agent for a variety of conditions including movement disorders, anxiety, and pain. In 2018 the United States Food and Drug Administration approved the CBD drug Epidiolex for the treatment of specific epilepsy disorders.

The chemical structure of CBD is:

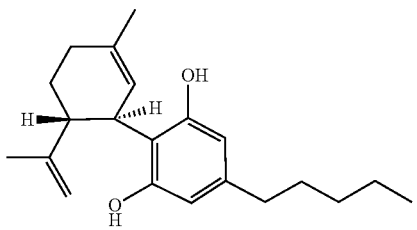 [SMILES: C=C(C)[C@@H]1CCC(C)=C[C@H]1c1c(O)cc(CCCCC)cc1O]

Cannabidiolic acid (CBDA) is the carboxylated precursor to CBD, and the compound present in *Cannabis* varieties. CBD is synthesized in the plant as acid forms (e.g., CBDA), and while some decarboxylation does occur in the plant, it increases significantly post-harvest and the kinetics increase at high temperatures.

The structure of CBDA is:

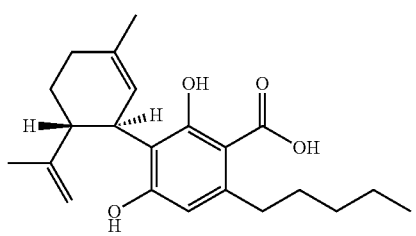 [SMILES: C=C(C)[C@@H]1CCC(C)=C[C@H]1c1c(O)cc(CCCCC)c(C(=O)O)c1O]

The Cultivar

NBS CBD-1 is a high CBD cultivar (>5%). The variety is an autoflower day-neutral strain, meaning it has a short time to maturity allowing for multiple growing cycles per year. The strain is commercially available under brands known as AutoCBD (Phylos Bioscience, Inc.) and Autopilot CBD.

Figure 5:
FIG. 5 is an image of the NBS CBD-1 variety.

NBS CBD-1 is visually uniform in habit, with all plants having a similar height and heavily branched structure. FIG. 5 is an illustration of an NBS CBD-1 plant. In addition, physiological maturity is similar for all plants with all plants maturing within a 5 day window.

Generation of the variety is described below in the Examples.

Sex expression: NBS CBD-1 is propagated as feminized seed, meaning>99.9 percent of the plants are genetically female.

Plant habit: NBS CBD-1 is heavily branching, with at least 4 heavy side branches.

Leaf shape: The leaflets of NBS CBD-1 are broad.

Pistil color: NBS CBD-1 will produce pink pistils.

Leaf shape: The average central leaflet length:width ratio of NBS CBD-1 is 4.7 with a standard deviation of 0.67.

Proportion female plants: >95%.

Natural plant height at flowering: 60 cm.

Branching: strong

Cotyledon shape: Medium Obovate

Cotyledon Color: Medium Green

Hypocotyl Intensity of Anthocyanin Coloration: Weak

Main stem color: Medium Green

Main stem length of Internode: Short

Main stem length of internode mean of 20: 9 cm

Main stem thickness: Medium

Main stem depth of grooves: Shallow

Main stem pith in cross-section: Medium

Plant anthocyanin coloration of crown: Absent or very weak.

Leaf intensity of green color: Medium

Leaf length of petiole: Medium

Leaf length of petiole mean of 20: 3.3 cm.

Leaf anthocyanin color in petiole: Absent or very weak

Leaf number of leaflets: medium (majority=7)

Central leaflet length: Medium

Central leaflet length mean of 20: 9.4 cm

Central leaflet width: Broad

Central leaflet width mean of 20: 2.1 mm

Seed color of testa: Grey brown

Seed color of testa color code: N199A

Seed marbling of color: Medium

Seed Shape: ovate

Seed sex: Feminized

Emergence: Approximately 80 days post emergence; not dependent upon photoperiod.

Pistil: Pink colored pistils before senescence.

*Cannabis* Breeding

*Cannabis* is an important and valuable crop. Thus, a continuing goal of *Cannabis* plant breeders is to develop stable, high yielding *Cannabis* cultivars that are agronomically sound. To accomplish this goal, the *Cannabis* breeder preferably selects and develops *Cannabis* plants with traits that result in superior cultivars. The plants described herein can be used to produce new plant varieties. In some embodiments, the plants are used to develop new, unique, and superior varieties or hybrids with desired phenotypes that are different from one or more of the parental strains.

The development of commercial *Cannabis* cultivars requires the development of *Cannabis* varieties, the crossing of these varieties, and the evaluation of the crosses. Pedigree breeding and recurrent selection breeding methods may be used to develop cultivars from breeding populations. Breeding programs may combine desirable traits from two or more varieties or various broad-based sources into breeding pools from which cultivars are developed by selfing and selection of desired phenotypes. The new cultivars may be crossed with other varieties and the hybrids from these crosses are evaluated to determine which have commercial potential.

First generation (F1) hybrid hemp seed produced by crossing a plant of the hemp variety NBS CBD-1 to a second hemp plant are provided. Also provided are the F1 hybrid hemp plants grown from hybrid seeds. A hybrid can refer to plants that are genetically different at any particular loci, and can further include a plant that is a variety that has been bred to have at least one phenotypically different characteristic from the parent, e.g., a progeny plant created from a cross between NBS CBD-1 and another plant wherein the hybrid progeny has at least one phenotypic characteristic that is different from the NBS CBD-1 variety.

Details of existing *Cannabis* plants varieties and breeding methods are described in Potter et al. (2011, World Wide Weed: Global Trends in *Cannabis* Cultivation and Its Control), Holland (2010, The Pot Book: A Complete Guide to *Cannabis*, Inner Traditions/Bear & Co, ISBN1594778981, 9781594778988), Green I (2009, The *Cannabis* Grow Bible: The Definitive Guide to Growing Marijuana for Recreational and Medical Use, Green Candy Press, 2009, ISBN 1931160589, 9781931160582), Green II (2005, The *Cannabis* Breeder's Bible: The Definitive Guide to Marijuana Genetics, *Cannabis* Botany and Creating Strains for the Seed Market, Green Candy Press, 1931160279, 9781931160278), Starks (1990, Marijuana Chemistry: Genetics, Processing & Potency, ISBN 0914171399, 9780914171393), Clarke (1981, Marijuana Botany, an Advanced Study: The Propagation and Breeding of Distinctive *Cannabis*, Ronin Publishing, ISBN 091417178X, 9780914171782), Short (2004, Cultivating Exceptional *Cannabis*: An Expert Breeder Shares His Secrets, ISBN 1936807122, 9781936807123), Cervantes (2004, Marijuana Horticulture: The Indoor/Outdoor Medical Grower's Bible, Van Patten Publishing, ISBN 187882323X, 9781878823236), Franck et al. (1990, Marijuana Grower's Guide, Red Eye Press, ISBN 0929349016, 9780929349015), Grotenhermen and Russo (2002, *Cannabis* and Cannabinoids: Pharmacology, Toxicology, and Therapeutic Potential, Psychology Press, ISBN 0789015080, 9780789015082), Rosenthal (2007, The Big Book of Buds: More Marijuana Varieties from the World's Great Seed Breeders, ISBN 1936807068, 9781936807062), Clarke, R C (*Cannabis*: Evolution and Ethnobotany 2013 (In press)), King, J (Cannabible Vols 1-3, 2001-2006), and four volumes of Rosenthal's Big Book of Buds series (2001, 2004, 2007, and 2011), each of which is herein incorporated by reference in its entirety for all purposes.

Pedigree selection, where both single plant selection and mass selection practices are employed, may be used for the generating varieties as described herein. Pedigree selection, also known as the "Vilmorin system of selection," is described in Fehr, Walter; Principles of Cultivar Development, Volume I, Macmillan Publishing Co., which is hereby incorporated by reference. Pedigree breeding is used commonly for the improvement of self-pollinating crops or inbred lines of cross-pollinating crops. Two parents which possess favorable, complementary traits are crossed to produce an F1. An F2 population is produced by selfing one or several F1's or by intercrossing two F1's (sib mating). Selection of the best individuals usually begins in the F2 population; then, beginning in the F3, the best individuals in the best families are usually selected. Replicated testing of families, or hybrid combinations involving individuals of these families, often follows in the F4 generation to improve the effectiveness of selection for traits with low heritability. At an advanced stage of inbreeding (e.g., F6 and F7), the best lines or mixtures of phenotypically similar lines are tested for potential release as new cultivars.

Choice of breeding or selection methods depends on the mode of plant reproduction, the heritability of the trait(s) being improved, and the type of cultivar used commercially (e.g., F1 hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

Mass and recurrent selections can be used to improve populations of either self- or cross-pollinating crops. A genetically variable population of heterozygous individuals may be identified or created by intercrossing several different parents. The best plants may be selected based on individual superiority, outstanding progeny, or excellent combining ability. Preferably, the selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent may be selected and repeatedly crossed (backcrossed) to the recurrent parent. The resulting plant is expected to have the attributes of the recurrent parent (e.g., cultivar) and the desirable trait transferred from the donor parent.

A single-seed descent procedure refers to planting a segregating population, harvesting a sample of one seed per plant, and using the one-seed sample to plant the next generation. When the population has advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

Mutation breeding is another method of introducing new traits into *Cannabis* varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company, 1993.

The complexity of inheritance also influences the choice of the breeding method. Backcross breeding may be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Molecular markers can also be used in breeding programs. Molecular markers can be designed and made, based on the genome of the plants of the present application. Non-limiting examples of molecular markers can be Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Single Nucleotide Polymorphisms (SNPs), Amplified Fragment Length Polymorphisms (AFLPs), and Simple Sequence Repeats (SSRs), which are also referred to as Microsatellites, etc. Methods of developing molecular markers and their applications are described by Avise (Molecular markers, natural history, and evolution, Publisher: Sinauer Associates, 2004, ISBN 0878930418, 9780878930418), Srivastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of which is incorporated by reference in its entirety for all purposes. Molecular markers can be used in molecular marker assisted breeding. For example, the molecular markers can be utilized to monitor the transfer of the genetic material. The transferred genetic material is a gene of interest, such as genes that contribute to one or more favorable agronomic phenotypes when expressed in a plant cell, a plant part, or a plant.

Isozyme Electrophoresis and RFLPs have been widely used to determine genetic composition. Shoemaker and Olsen, (Molecular Linkage Map of Soybean (Glycine max) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Additional breeding methods have been known to one of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, Publisher: READ BOOKS, 2007, ISBN1406737062, 9781406737066), each of which is incorporated by reference in its entirety for all purposes. *Cannabis* genome has been sequenced (Bakel et al., The draft genome and transcriptome of *Cannabis sativa*, Genome Biology, 12 (10):R102, 2011). Molecular markers for *Cannabis* plants are described in Datwyler et al. (Genetic variation in hemp and marijuana (*Cannabis sativa* L.) according to amplified fragment length polymorphisms, J Forensic Sci. 2006 March; 51 (2):371-5), Pinarkara et al., (RAPD analysis of seized marijuana (*Cannabis sativa* L.) in Turkey, Electronic Journal of Biotechnology, 12 (1), 2009), Hakki et al., (Inter simple sequence repeats separate efficiently hemp from marijuana (*Cannabis sativa* L.), Electronic Journal of Biotechnology, 10 (4), 2007), Datwyler et al., (Genetic Variation in Hemp and Marijuana (*Cannabis sativa* L.) According to Amplified Fragment Length Polymorphisms, J Forensic Sci, March 2006, 51 (2):371-375), Gilmore et al. (Isolation of microsatellite markers in *Cannabis sativa* L. (marijuana), Molecular Ecology Notes, 3 (1):105-107, March 2003), Pacifico et al., (Genetics and marker-assisted selection of chemotype in *Cannabis sativa* L.), Molecular Breeding (2006) 17:257-268), and Mendoza et al., (Genetic individualization of *Cannabis sativa* by a short tandem repeat multiplex system, Anal Bioanal Chem (2009) 393:719-726), each of which is herein incorporated by reference in its entirety for all purposes.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

The present invention describes numerous embodiments of a hemp plant variety designated NBS CBD-1. In an embodiment, a seed of a hemp plant variety designated NBS CBD-1 is provided. In an embodiment, a hemp plant is provided. The hemp plant comprises at least one plant cell produced by growing the seed of a hemp plant variety designated NBS CBD-1. In an embodiment an F1 hybrid seed is provided. The hybrid seed is produced by crossing the hemp plant of variety NBS CBD-1 with a different hemp plant. In an embodiment, an F1 hybrid plant or plant part grown from a seed of an F1 hybrid of a plant of variety NBS CBD-1 is provided. In an embodiment a tissue culture of cells is provided. The tissue culture of cells is produced from a hemp plant of the variety NBS CBD-1. In an embodiment a protoplast is provided. The protoplast is produced from a hemp plant of the variety NBS CBD-1. In an embodiment a method of generating processed hemp is provided. The method comprises the use of a plant of the variety NBS CBD-1. In an embodiment of the hemp product is a CBD product. In an embodiment a hemp product is provided. The hemp product is produced using a plant of the variety NBS CBD-1. In an embodiment the hemp product is a CBD product.

Methods of Use

The present invention provides methods of using the *Cannabis* plants or any parts, any compositions, or any chemicals derived from said plants of the present invention. *Cannabis* oil extracts can be used in the manufacture of a pharmaceutical composition or for a medicament for treating a number of conditions.

The plants can also be used for non-medical purposes. In some embodiments the specialty *Cannabis* plants of the present invention can be used for recreational purposes. In some embodiments, the specialty *Cannabis* plants of the present invention can be used for industrial purposes. In some embodiments, the plants are used for producing food, oil, wax, resin, rope, cloth, pulp, fiber, feed for livestock, construction material, plastic and composite materials, paper, jewelry, water and soil purification materials, weed control materials, cultivation materials, textiles, clothing, biodegradable plastics, body products, health food and biofuel.

Tissue Culture

Further reproduction of the variety can occur by tissue culture and regeneration. As is well known in the art, tissue culture of *Cannabis* can be used for the in vitro regeneration of a *Cannabis* plant. Tissue culture of various tissues of *Cannabis* and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672. It is clear from the literature that the state of the art is such that these methods of obtaining plants are, and were, "conventional" in the sense that they are routinely used and have a very high rate of success. Thus, another aspect of this invention is to provide cells which upon growth and differentiation produce *Cannabis* plants having the physiological and morphological characteristics of variety PBI-0227-CMV.

EXAMPLE

Variety NBS CBD-1

The creation and genealogy of NBS CBD-1 is as follows: NBS CBD-1 was first increased from 50 plants of selection 17-2-6-17 in July 2018. 17-2-6-17 was selected in April 2018 for uniformity and CBD content from within a group of 29 F3 families (17-2-6) that were segregating for CBD content and flower color. The 29 F3 families (17-2-6) were generated by selfing plants from F2 family (16-2-11-6) during July 2017. The F2 family (16-2-11-6) was selected from within 28 families segregating for CBD content (16-2-11) during April 2017. The 28 F2 families (16-2-11) were generated by selfing individual plants from an intercrossing population of day neutral *Cannabis* generated July 2016 (seed lot 160111). Subsequent to the creation of seed lot 180209, stock seed was increased in October 2018. Selection was performed on stock seed to remove minor off-types. Stock seed was further increased in March 2019 to generate commercial seed, again with selection against minor off types.

NBS CBD-1 is visually uniform in habit, with all plants having a similar height and heavily branched structure. In addition, physiological maturity is similar for all plants with all plants maturing within a 5 day window. NBS CBD-1 has been increased twice from the initial seed lot with minimal removal of off-type plants. No variation in habit, maturity or CBD content has been observed during these two increases Genetic Analyses of NBS CBD-1

Figure 2:
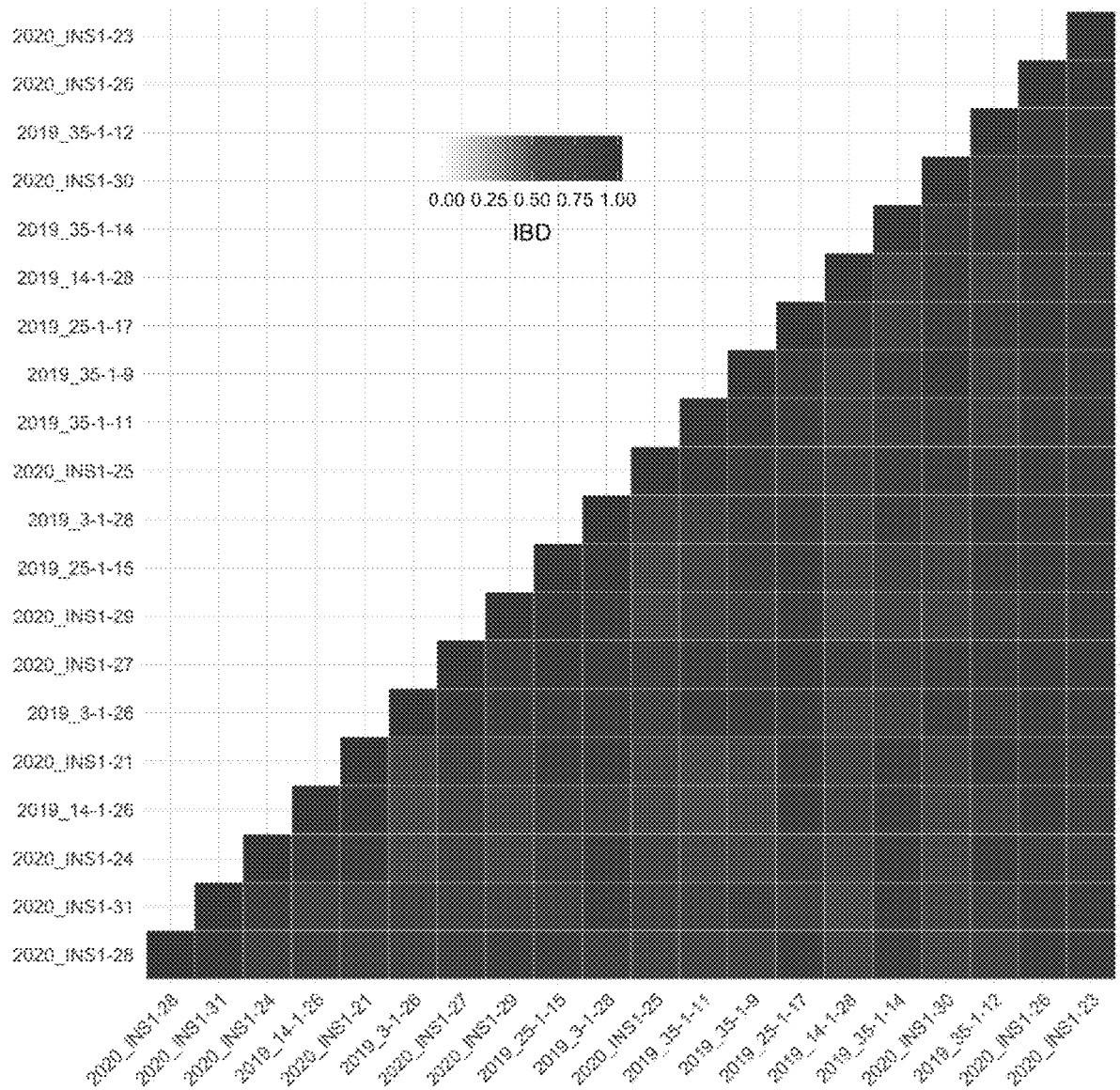
FIG. 2 illustrates pairwise genetic identity for a collection of twenty NBS CBD-1 samples, each of which are described on both the X and Y axes.
Figure 3:
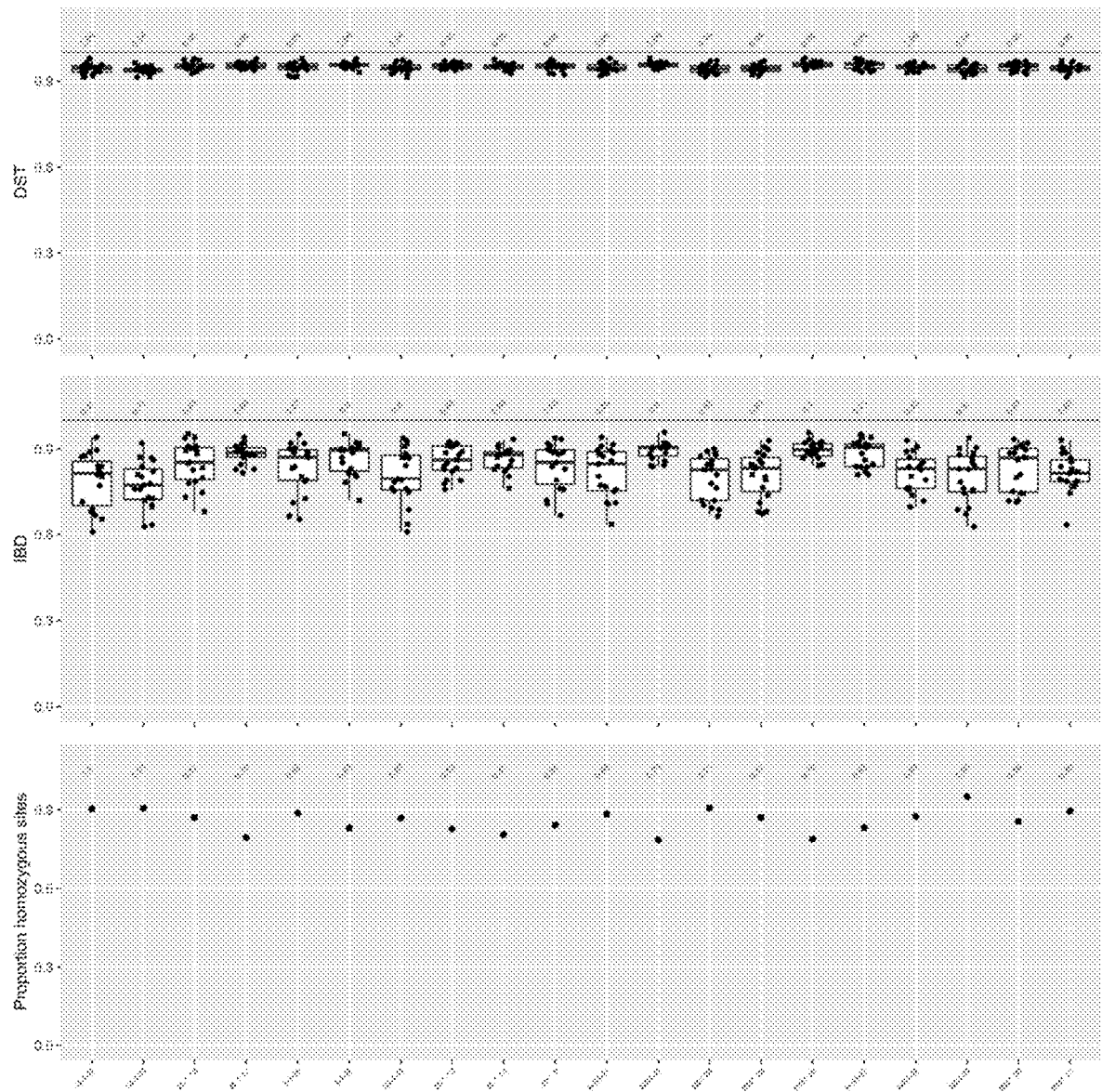
FIG. 3 provides boxplot illustrations of the genetic distances or identity of the twenty NBS CBD-1 samples illustrated in FIGS. 1 and 2. The top panel provides plots of pairwise genetic distance per sample. The middle panel provides plots of pairwise genetic identity per sample. The bottom panel illustrates genetic variation via proportion of homozygous sites.
Figure 4:
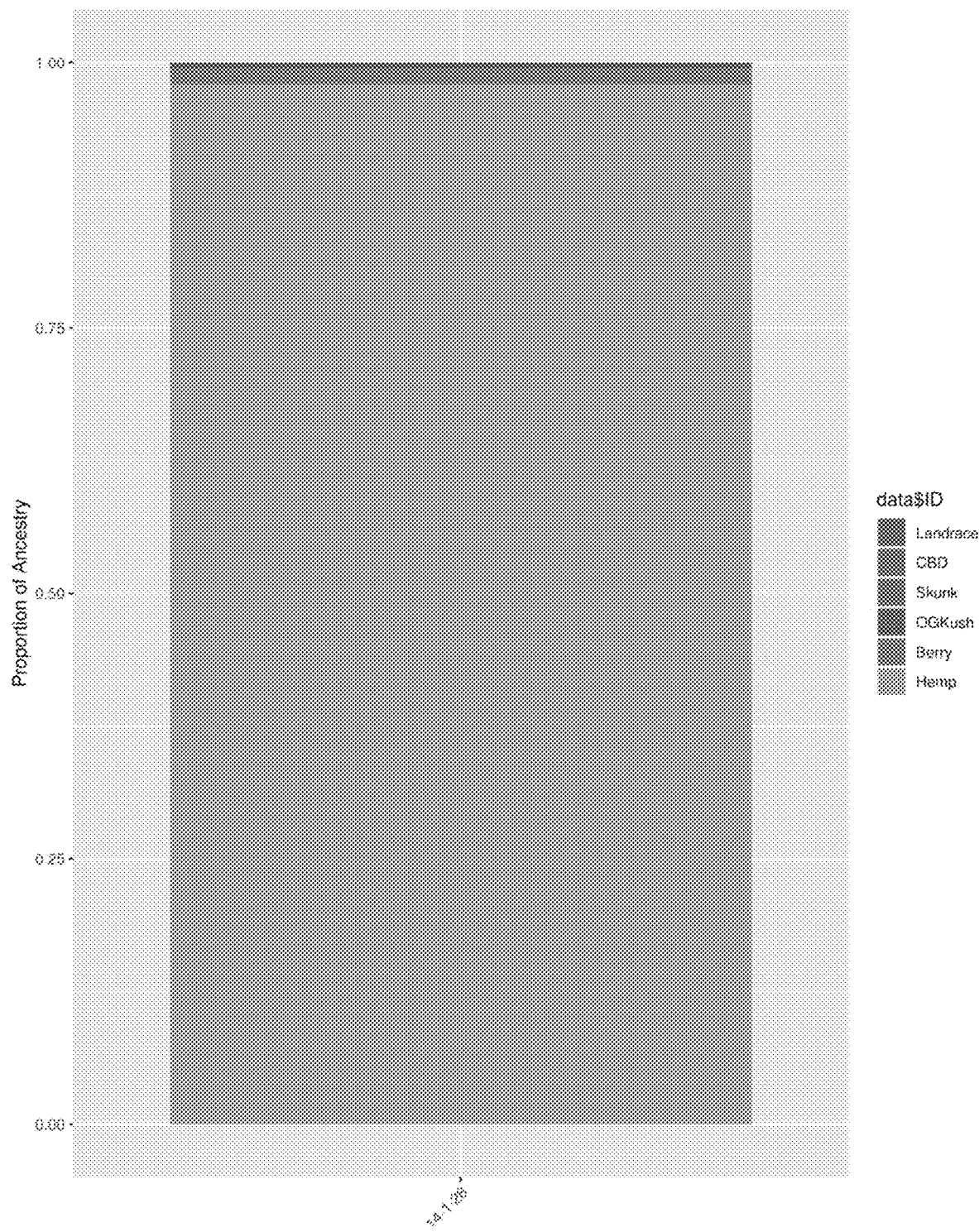
FIG. 4 illustrates a stacked bar plot demonstrating the genetic profile of NBS CBD-1 (labelled "hemp") against different *Cannabis* varieties.

Genetic analysis of NBS CBD-1 was conducted in-house at Phylos Bioscience, Inc. The pairwise genetic distance for a collection of twenty NBS CBD-1 samples is illustrated in FIG. 1. The pairwise genetic identity for a collection of twenty NBS CBD-1 samples is illustrated in FIG. 1. FIG. 3 provides boxplot illustrations of the genetic distances or identity of the twenty NBS CBD-1 samples illustrated in FIGS. 1 and 2, as well as genetic variation via proportion of homozygous sites. The genetic profile of NBS CBD-1 was further compared against different *Cannabis* varieties (FIG. 4).

Following genotyping NBS CBD-1 was entered into the Phylos Galaxy, which provides a genetic comparison of *Cannabis* and hemp varieties. The Galaxy ID is GAL289314, and the genotype ID is G-SLZNB. The public genotype report can be found at https://phylos.bio/sims/sample/genotype/d8vx37ng. NBS CBD-1 shows a very high level of homozygosity, indicating high genetic uniqueness.

Deposit Information

A deposit of the hemp cultivar NBS CBD-1, which is disclosed herein above and referenced in the claims, will be made with the American Type Culture Collection (ATCC). The date of deposit is Aug. 6, 2020 and the accession number for those deposited seeds of hemp cultivar NBS CBD-1 is ATCC Accession No. PTA-126807. All restrictions upon the deposit have been removed, and the deposit is intended to meet all of the requirements of the Budapest Treaty and 37 C.F.R. § 1.801-1.809. The deposit will be maintained in the depository for a period of 30 years, or 5 years after the last request, or for the effective life of the patent, whichever is longer, and will be replaced if necessary during that period. Applicant does not waive any infringement of rights granted under this patent or under the Plant Variety Protection Act (7 USC 2321 et seq.).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

What is claimed is:

1. A hemp plant of a variety designated NBS CBD-1, wherein a representative sample of seed of said plant has been deposited under American Type Culture Collection ("ATCC") Accession No. PTA-126807.

2. A seed of a hemp plant of a variety designated NBS CBD-1, wherein a representative sample of seed of said plant cultivar has been deposited under ATCC Accession No. PTA-126807.

3. The seed of claim 2, further comprising a trait introduced by backcrossing or genetic transformation.

4. A hemp plant, or part thereof, including at least one plant cell, produced by growing the seed of claim 2.

5. An F1 hybrid seed produced by crossing the hemp plant of claim 1 with a different hemp plant.

6. An F1 hybrid plant grown from the seed of claim 5, or a plant part thereof, the plant part comprising at least one cell of the F1 hybrid plant.

7. A tissue culture of cells produced from the hemp plant of claim 1.

8. A hemp plant generated from the tissue culture of claim 7, wherein the plant has all of the morphological and physiological characteristics of variety NBS CBD-1, wherein a representative sample of seed of said plant has been deposited under ATCC Accession No. PTA-126807.

9. A protoplast produced from the hemp plant of claim 1.

10. A method of generating a processed hemp product comprising collecting a plant or plant part thereof, of variety NBS CBD-1, and producing a processed hemp product from the plant or plant product thereof, wherein a representative sample of seed of said variety has been deposited under ATCC Accession Number PTA-126807.

11. The method of claim 10, wherein the hemp product is a CBD product.

* * * * *